United States Patent
Chen

(10) Patent No.: US 6,696,605 B2
(45) Date of Patent: Feb. 24, 2004

(54) PROCESS FOR PREPARING α-HYDROXYAMIDES AND α-KETOAMIDES ON A SOLID PHASE SUPPORT

(75) Inventor: Jian Chen, Mason, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 10/335,782

(22) Filed: Jan. 1, 2003

(65) Prior Publication Data

US 2003/0176739 A1 Sep. 18, 2003

Related U.S. Application Data

(60) Provisional application No. 60/360,410, filed on Feb. 28, 2002.

(51) Int. Cl.$^7$ .............................. C07C 231/06
(52) U.S. Cl. ....................... 564/124; 564/169; 564/199; 564/163; 564/193
(58) Field of Search ................. 564/124, 163, 564/169, 193, 199

(56) References Cited

PUBLICATIONS

Chen et al, Tetrahedron letters, Vol 42, pp. 2269–2271, 2001.*
Semple et al, Organic Letters, Vol 2, No. 18, pp. 2769–2772, 2000.*

* cited by examiner

Primary Examiner—Shailendra Kumar
(74) Attorney, Agent, or Firm—Richard S. Echler, Sr.

(57) ABSTRACT

The present invention relates to a process for preparing a α-hydroxyamide or α-ketoamide, said process comprising the steps of:
  a) reacting a resin which comprises a polymer-supported isocyanide with an aldehyde in the presence of a catalyst, to form a resin-bound α-hydroxyamide;
  b) optionally reacting said resin-bound α-hydroxyamide with a reagent which is capable of oxidizing said resin-bound α-hydroxyamide to a resin-bound α-ketoamide; and
  c) reacting said resin-bound α-hydroxyamide or resin-bound α-ketoamide with a reagent which cleaves the nitrogen-resin bond to form a α-hydroxyamide α-ketoamide.

34 Claims, No Drawings

PROCESS FOR PREPARING α-HYDROXYAMIDES AND α-KETOAMIDES ON A SOLID PHASE SUPPORT

CROSS REFERENCE TO RELATED APPLICATIONS

This application claims priority under Title 35, United States Code 119(e) from Provisional Application Ser. No. 60/360,410 filed Feb. 28, 2002.

FIELD OF THE INVENTION

The present invention relates to a process for the preparation of resin-bound α-hydroxyamides and α-ketoamides which is adaptable for the preparation of Combinatorial Chemical Libraries.

BACKGROUND OF THE INVENTION

Polymer resin-bound substrates have been used for peptide synthesis since R. B. Merrifield first described his methodology for chemical synthesis on a solid matrix. In fact, resin-bound reactions have become ubiquitous toward the application of Combinatorial Libraries.

Isocyanides are reagents which are useful for the preparation of many nitrogen containing cyclic and acyclic compounds. I. Ugi et al., have used these reagents to prepare compounds under multicomponent reaction (MCR) conditions, for example, in the 4 component Ugi Reaction first described in 1959 (I. Ugi et al., *Angew. Chem.*, 1959, 71, 386). However, the simple use of isocyanide as a means for converting aldehydes to α-hydroxyamides and α-ketoamides on a solid phase resin has heretofore not been described.

There is a long felt need for a means for preparing α-hydroxy-amides and α-ketoamides in a manner which is adaptable to solid state synthetic procedures, as well as Combinatorial Libraries.

SUMMARY OF THE INVENTION

The present invention meets the aforementioned need in that it has been surprisingly discovered that the isocyanide functional group can be used as a reagent for a carbon-nitrogen two-atom homologation reaction which produces α-hydroxyamides. In addition, this reaction can be extended to accomplish the solid phase preparation of α-ketoamides.

The first aspect of the present invention relates to a process for preparing a α-hydroxyamide, said process comprising the steps of:

a) reacting a resin which comprises a polymer-supported isocyanide having the formula:

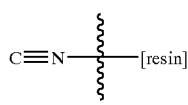

with an aldehyde having the formula:

in the presence of a catalyst, to form a resin-bound α-hydroxyamide having the formula:

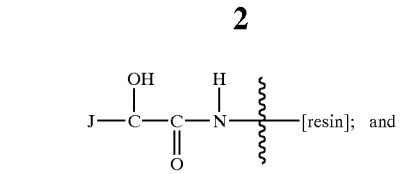

b) reacting said resin-bound α-hydroxyamide with a reagent which cleaves the nitrogen-resin bond to form a α-hydroxyamide having the formula:

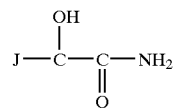

wherein J is a compatible organic radical which is not capable of reacting with said resin which comprises a polymer-supported isocyanide in step (a).

The second aspect of the present invention relates to a process for preparing a α-ketoamide, said process comprising the steps of:

a) reacting a resin which comprises a polymer-supported isocyanide having the formula:

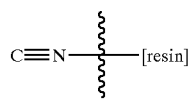

with an aldehyde having the formula:

in the presence of a catalyst, to form a resin-bound α-hydroxyamide having the formula:

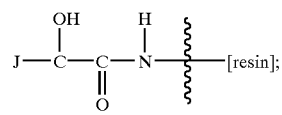

b) oxidizing said resin-bound α-hydroxyamide to a α-ketoamide having the formula:

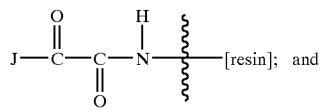

c) reacting said resin-bound α-ketoamide with a reagent which cleaves the nitrogen-resin bond to form a α-ketoamide having the formula:

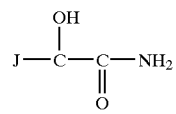

wherein J is a compatible organic radical which is not capable of reacting with said resin which comprises a polymer-supported isocyanide in step (a).

DETAILED DESCRIPTION OF THE INVENTION

The present invention relates to a process for preparing α-hydroxyamides and α-ketoamides. The process of the present invention can be adapted to the preparation of any α-hydroxyamides or α-ketoamides, including amino acids and other nitrogen atom containing synthetic intermediates. The process of the present invention is especially useful for introducing a α-hydroxy amido or α-keto amido functionality into molecules having base sensitive protecting groups.

For the purposes of the present invention the term "hydrocarbyl" is defined herein as any organic unit or moiety which is comprised of carbon atoms and hydrogen atoms. Included within the term hydrocarbyl are the heterocycles which are described herein below. Examples of various non-heterocyclic hydrocarbyl units include pentyl, 3-ethyloctanyl, 1,3-dimethylphenyl, cyclohexyl, cis-3-hexyl, 7,7-dimethylbicyclo[2.2.1]heptan-1-yl, and naphth-2-yl.

Included within the definition of "hydrocarbyl" are the aromatic (aryl) and non-aromatic carbocyclic rings, non-limiting examples of which include cyclopropyl, cyclobutyl, cyclopentyl, cyclohexyl, cyclohexenyl, cycloheptyl, bicyclo-[0.1.1]-butanyl, bicyclo-[0.1.2]-pentanyl, bicyclo-[0.1.3]-hexanyl (thujanyl), bicyclo-[0.2.2]-hexanyl, bicyclo-[0.1.4]-heptanyl (caranyl), bicyclo-[2.2.1]-heptanyl (norboranyl), bicyclo-[0.2.4]-octanyl (caryophyllenyl), spiropentanyl, diclyclopentanespiranyl, decalinyl, phenyl, benzyl, naphthyl, indenyl, 2H-indenyl, azulenyl, phenanthryl, anthryl, fluorenyl, acenaphthylenyl, 1,2,3,4-tetrahydronaphthalenyl, and the like.

The term "heterocycle" includes both aromatic (heteroaryl) and non-aromatic heterocyclic rings non-limiting examples of which include: pyrrolyl, 2H-pyrrolyl, 3H-pyrrolyl, pyrazolyl, 2H-imidazolyl, 1,2,3-triazolyl, 1,2,4-triazolyl, isoxazolyl, oxazoyl, 1,2,4-oxadiazolyl, 2H-pyranyl, 4H-pyranyl, 2H-pyran-2-one-yl, pyridinyl, pyridazinyl, pyrimidinyl, pyrazinyl, piperazinyl, s-triazinyl, 4H-1,2-oxazinyl, 2H-1,3-oxazinyl, 1,4-oxazinyl, morpholinyl, azepinyl, oxepinyl, 4H-1,2-diazepinyl, indenyl 2H-indenyl, benzofuranyl, isobenzofuranyl, indolyl, 3H-indolyl, 1H-indolyl, benzoxazolyl, 2H-1-benzopyranyl, quinolinyl, isoquinolinyl, quinazolinyl, 2H-1,4-benzoxazinyl, pyrrolidinyl, pyrrolinyl, quinoxalinyl, pyrrolyl, furanyl, thiophenyl, benzimidazolyl, and the like each of which can be substituted or unsubstituted. A non-limiting example of a $C_1$ heterocycle is tetrazole The term "substituted" is used throughout the specification. The term "substituted" is defined herein as "encompassing moieties or units which can replace a hydrogen atom, two hydrogen atoms, or three hydrogen atoms of a hydrocarbyl moiety. Also the term "substituted" can include replacement of hydrogen atoms on two adjacent carbons to form a new moiety or unit." For example, a substituted unit that requires a single hydrogen atom replacement includes halogen, hydroxyl, and the like. A two-hydrogen atom replacement includes carbonyl, oximino, and the like. A two-hydrogen atom replacement from adjacent carbon atoms includes epoxy, and the like. Threehydrogen replacement includes cyano, and the like. The term "substituted" is used throughout the present specification to indicate that a hydrocarbyl moiety, inter alia, aromatic ring, alkyl chain, can have one or more of the hydrogen atoms replaced by a substituent. When a hydrocarbyl unit is described as "substituted" any number of the hydrogen atoms may be replaced. For example, 4-hydroxyphenyl is a "substituted aromatic carbocyclic ring", (N,N-dimethyl-5-amino)octanyl is a "substituted $C_8$ alkyl unit, 3-guanidinopropyl is a "substituted $C_3$ alkyl unit," and 2-carboxypyridinyl is a "substituted heteroaryl unit." There may also be substitutions at more than one carbon atom in a hydrocarbyl moiety, for example, 3,5-difluorobenzene, and 2,3-dihydroxybutane. The following are non-limiting examples of units which can serve as a replacement for hydrogen atoms when a hydrocarbyl unit is described as "substituted."

i) —$[C(R^4)_2]_p(CH=CH)_qR^4$; wherein p is from 0 to 12; q is from 0 to 12;
ii) —$C(X)R^4$;
iii) —$C(X)_2R^4$;
iv) —$C(X)CH=CH_2$;
v) —$C(X)N(R^4)_2$;
vi) —$C(X)NR^4N(R^4)_2$;
vii) —CN;
viii) —CNO;
ix) —$CF_3$, —$CCl_3$, —$CBr_3$;
x) —$N(R^4)_2$;
xi) —$NR^4CN$;
xii) —$NR^4C(X)R^4$;
xiii) —$NR^4C(X)N(R^4)_2$;
xiv) —$NHN(R^4)_2$;
xv) —$NHOR^4$;
xvi) =$NOR^4$;
xvii) —NCS;
xviii) —$NO_2$;
xix) —$OR^4$;
xx) —OCN;
xxi) —$OCF_3$, —$OCCl_3$, —$OCBr_3$;
xxii) —F, —Cl, —Br, —I, and mixtures thereof;
xxiii) —SCN;
xxiv) —$SO_3M$;
xxv) —$OSO_3M$;
xxvi) —$SO_2N(R^4)_2$;
xxvii) —$SO_2R^4$;
xxviii) —$P(O)H_2$;
xxix) —$PO_2$;
xxx) —$P(O)(OH)_2$;
xxxi) and mixtures thereof;

wherein $R^4$ is hydrogen, substituted or unsubstituted $C_1$–$C_{20}$ linear, branched, or cyclic alkyl, $C_6$–$C_{20}$ aryl, $C_7$–$C_{20}$ alkylenearyl, and mixtures thereof; M is hydrogen, or a salt forming cation; X is oxygen, sulfur, =$NR^4$, and mixtures thereof. Suitable salt forming cations include, sodium, lithium, potassium, calcium, magnesium, ammonium, and the like. Non-limiting examples of an alkylenearyl unit include benzyl, 2-phenylethyl, 3-phenylpropyl, 2-phenylpropyl.

Formation of α-Hydroxyamides

The process of the present invention, which provides for the synthetic transformation of an aldehyde to a two atom homologated α-hydroxyamide, is depicted in the following general scheme:

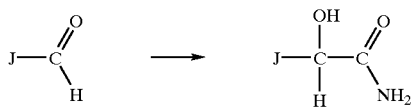

wherein J represents a compatible organic radical. The term "compatible organic radical" is defined herein as a hydrocarbyl unit which is not capable of reacting with the resin bound isocyanide moiety.

In general, the first aspect of the present invention comprises the steps of:

a) reacting a resin which comprises a polymer-supported isocyanide having the formula:

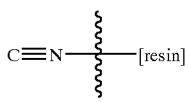

with an aldehyde having the formula:

in the presence of a catalyst, to form a resin-bound α-hydroxyamide having the formula:

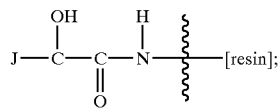

and b) reacting said resin-bound α-hydroxyamide with a reagent which cleaves the nitrogen-resin bond to form a α-hydroxyamide having the formula:

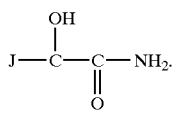

Resin Comprising a Polymer-Supported Isocyanide

Step (a) of each aspect of the present invention relates to the reaction of a "resin comprising polymer-supported isocyanide" with an aldehyde unit. Any high molecular weight polymer which can be modified to comprise an isocyanide moiety is suitable for use in the present process.

One embodiment is to provide a hydroxyl unit comprising polystyrene resin, inter alia, Merrifield resin, Wang resin and react this resin with a molecule which can be readily converted to an isocyanide, for example, an amino acid which can be converted to an isocyanide by the procedure described herein below. Another embodiment for providing a resin comprising an isocyanide is to chemically modify a resin having an existing amino group, inter alia, a Rink resin.

Step (a)

Step (a) of the present invention comprises the step of reacting an aldehyde with a resin which comprises a polymer-supported isocyanide in the presence of a catalyst to form a resin-bound α-hydroxyamide.

One embodiment relates to catalyst systems which comprise trifluoroacetic acid and an organic base. Non-limiting examples of suitable bases are selected from the group consisting of substituted or unsubstituted pyridine, piperidine, lutidine, s-triazine, and salts thereof.

Step (a) may be conducted in the presence of a solvent, one iteration of which is to utilize a non-polar solvent. Non-limiting examples of suitable solvents are those which are selected from the group consisting of dichloromethane ($CH_2Cl_2$), dichloroethane ($C_2H_4Cl_2$), 1,1,1-trichloro-ethane ($CCl_3CH_3$), carbon tetrachloride ($CCl_4$), chloroform ($CHCl_3$), benzene, toluene, xylene, tetrahydrofuran (THF), diethyl ether, and mixtures thereof. One embodiment of the present invention utilizes $CH_2Cl_2$ as a solvent for both the reaction performed in step (a), as well as a means for pre-swelling the resin prior to usage.

Step (a) of the present invention can be conducted at any temperature ranging from −78° C. to 25° C. (ambient temperature). However, different embodiments will require varying the temperature range depending upon reactivity of the aldehyde and isocyanide resin. One iteration of step (a) is conducted at a temperature of from −78° C. to 0° C., while another iteration is conducted at a temperature of from −15° C. to 25° C. One embodiment of step (a) includes first combining the reactants at a temperature of −15° C. and allowing the reactants to warm to 0° C. over time. This embodiment can be extended to allow the reactants to warm to ambient temperature (25° C.).

Step (a) can be conducted under an inert atmosphere when desirable. Any source of inert gas, inter alia, dry nitrogen or argon is suitable for use in conducting step (a).

The first aspect of the present invention relates to the formation of α-hydroxyamides, however, both the first and second aspects of the present invention have step (a) in common. The only differences which may arise between the first and second aspects of the present invention may relate to the degree to which the product of step (a) is isolated. The second step of the second aspect is the oxidation of the hydroxyamide to the ketoamide and the chosen means for this oxidation may require a more rigorous isolation than would be required if only the cleavage reaction remained.

One embodiment of the first aspect of the present invention relates to the formation of a α-hydroxyamide which comprises a nitrogen-containing functionality other than the amide nitrogen which is introduced into the molecule via step (a). One iteration relates to α-hydroxyamides have the formula:

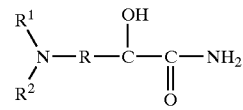

wherein R is a unit having the formula:

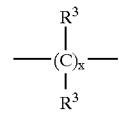

each $R^1$, $R^2$, and $R^3$ are independently hydrogen, $C_1$–$C_{20}$ substituted or unsubstituted hydrocarbyl, $C_1$–$C_{20}$ substituted or unsubstituted heterocyclic, and mixtures thereof; $R^1$ and $R^2$ can be taken together to form a single $C_1$–$C_{20}$ substituted or unsubstituted hydrocarbyl or $C_1$–$C_{20}$ substituted or unsubstituted heterocyclic unit; the index x is from 1 to 20.

Another iteration of this aspect relates to the use of the present process as part of an overall scheme to convert an amino acid to the corresponding α-hydroxyamide or α-ketoamide. As it relates to this iteration (α-amino acids) one $R^3$ is hydrogen and while the other $R^3$ unit is selected from the group consisting of hydrogen (glycine), methyl (alanine), 1-methylethyl (valine), 2-methylpropyl (leucine), 1-methylpropyl (isoleucine), amidomethyl (asparagine), 2-amidoethyl (glutamine), 2-mercaptoethyl (cysteine), 2-methythioethyl (methionine), 3-guanidinopropyl (arginine), carboxymethyl (aspartic acid), 2-carboxyethyl (glutamic acid), 3-aminopropyl (ornithine), 4-aminobutyl (lysine), hydroxymethyl (serine), 1-hydroxyethyl (threonine), (4-imidazolyl)methyl (histidine), (3-indolyl) methyl (tryptophan), benzyl (phenylalanine), and 4-hydroxybenzyl (tyrosine). For this iteration the index x is equal to one.

This iteration of the first aspect typically requires protection of the amino group nitrogen with a protecting group that is not acid labile. One embodiment is to utilize nitrogen protecting such carbobenzyloxy, 9-fluorenyl-methoxycarbonyl, 9-(2-sulfo)fluorenyl-methoxycarbonyl, or benzyl. Another embodiment utilizes protecting groups such as phthalimido wherein $R^1$ and $R^2$ are taken together to form a $C_8$ aryl hydrocarbyl unit, for example, a starting material aldehyde having the formula:

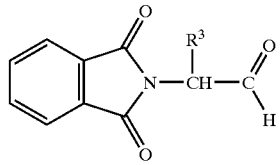

wherein $R^3$ is an amino acid side chain.

Another iteration of the present invention relates to conducting step (a) under phase transfer conditions. For example, step (a) can be modified to comprise:

a) suspending a resin which comprises a polymer-supported isocyanide in a non-polar solvent comprising a catalyst to form a non-aqueous phase, dissolving an amino aldehyde in water comprising a phase transfer catalyst to form an aqueous phase, and contacting said non-aqueous phase with said aqueous phase to form a resin-bound α-hydroxyamide.

Step (b)

Step (b) of the first aspect of the present invention comprises the step of reacting a resin-bound α-hydroxyamide formed in step (a) with a reagent which is effective in cleaving the nitrogen-resin chemical bond thereby releasing a α-hydroxyamide.

In one iteration of step (b) the nitrogen-resin is cleaved by a system comprising:

i) from 15% to 95% by volume, of trifluoroacetic acid; and ii) a carbocation scavenger.

Depending upon the embodiment, the formulator will adjust the amount of trifluoroacetic acid which is necessary to complete the fragmentation reaction. The carbocation scavenger can be any reagent which will quench the carbocation which is formed during the course of the reaction of step (b). Non-limiting examples of a scavenger is selected from the group consisting of dimethyl silane, triisopropylsilane, and mixtures thereof.

Step (b) may be conducted in the presence of a solvent, one iteration of which is to utilize a non-polar solvent. Non-limiting examples of suitable solvents are those which are selected from the group consisting of dichloromethane ($CH_2Cl_2$), dichloroethane ($C_2H_4Cl_2$), 1,1,1-trichloro-ethane ($CCl_3CH_3$), carbon tetrachloride ($CCl_4$), chloroform ($CHCl_3$), benzene, toluene, xylene, tetrahydrofuran (THF), diethyl ether and mixtures thereof. One embodiment of the present invention utilizes $CH_2Cl_2$ as a solvent.

The second aspect of the present invention relates to the inclusion of the optional step of oxidizing the α-hydroxyamide which is formed in step (a) having the formula:

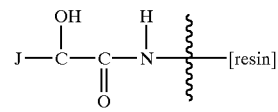

with an oxidizing agent to form a α-ketoamide having the formula:

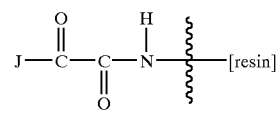

prior to cleavage from the resin. The oxidation can be conducted with any suitable oxidizing agent, including by way of enzymatic oxidation. Non-limiting examples of oxidizing agent are selected from the group consisting of (1,1,1-triacetoxy)-1,1-dihydro-1,2-benziodoxol-3(1H)-one (Dess-Martin reagent), pyridine sulfoxide, 2,2,6,6-tetramethyl-1-piperidinyloxy free radical (TEMPO), sodium hypochlorite, pyridinium dichromate, pyridinium chlorochromate, DMSO/oxalyl chloride (Swern oxidation), 2,3-dichloro-5,6-dicyano-1,4-benzoquinone (DDQ), and mixtures thereof.

As it relates to the second aspect of the present invention, the formation of the resin-bound α-hydroxyamide and cleavage reaction are the same.

EXAMPLE 1

General Procedure for Preparing a Resin Comprising a Polymer-supported Isocyanide Rink resin is deprotected and suspended in $CH_2Cl_2$. The suspension is cooled in ice and pyridine (1 equivalent) and $HCO_2H$ (5 equivalents) are added followed by the addition of diisopropylcarbodiimide (DIC) (5 equivalents). The suspension is stirred fro 1 hour at 0° C. and allowed to warm to room temperature and continue stirring until the coupling is judged complete. (One convenient means for judging coupling completeness relates to the procedure described in *Anal. Biochem.*, Kaiser et al., 1970, 34, 595–598 incorporated herein by reference). The resin is then washed in N,N-dimethylformamide, methanol, dichloromethane and dried to produce a formylated Rink resin.

The formylated resin is suspended in anhydrous dichloromethane and cooled in an ice bath under inert atmosphere. Diisopropylethylamine (DIEPA) (15 equivalents) is cannulated into the suspension. Phosphorous oxychloride (5 equivalents) is then added slowly in portions. The suspension is stirred 5 hours in at ice bath temperature then allowed to warm to room temperature and stir an additional 1 hour. The resulting resin is then washed with dichloromethane and ether followed by drying in vacuo to a constant weight to form a modified Rink resin.

EXAMPLE 2

Coupling of Amino Aldehyde to a Modified Rink Resin

Fmoc-Asp(O $^t$Bu)-H (7.66 g, 19.37 mmol) is dissolved in anhydrous dichloromethane (80 mL) and the solution is added to an equivalent amount of the modified Rink resin from EXAMPLE 1. The resulting suspension is cooled to −78° C. and pyridine (1.57 mL, 19.37 mmol) is added, followed by pyridinium trifluoroacetate (3.74 g, 19.37 mmol) which has been dissolved in dichloromethane (20 mL). The suspension is stirred at 0° C. for 1 hour than at room temperature for 16 hours. The resin is washed with N,N-dimethylformamide, methanol, then DMF and is used in the next step without further purification.

EXAMPLE 3

Removal of 9-fluorenylmethoxycarbonyl (Fmoc) Unit

The coupled resin from EXAMPLE 2 is agitated in a solution of 20% piperidine in N,N-dimethylformamide for 30 minutes, The resulting deprotected coupled resin is the sequentially washed with N,N-dimethylformamide, methanol, dichloromethane, then methanol. The coupled resin is dried in vacuo prior to the next step.

EXAMPLE 4

Acylation of a Resin-linked α-hydroxyamide

The coupled resin from EXAMPLE 3 (0.25 g, 0.175 mmol) is washed with anhydrous $CH_2Cl_2$ and the resin agitated in a 1:1 mixture of dichloromethane and N,N-dimethylformamide containing 4-biphenylcarboxylic acid (0.052 g, 0.263 mmol) and 1-(3-dimethylaminopropyl)-3-ethyl-carbodiimide hydrochloride (0.050 g, 0.263 mmol) for 24 hours. The resulting acylated resin-coupled adduct is then washed with N,N-dimethylformamide, methanol, dichloromethane, then methanol before drying in vacuo.

EXAMPLE 5

Dess-Martin Oxidation of a α-hydroxyamide to a α-ketoamide

The resin bound α-hydroxyamide from EXAMPLE 4 (0.25 g, 0.175 mmol) is washed with anhydrous dichloromethane. (1,1,1-Triacetoxy)-1,1-dihydro-1,2-benziodoxol-3(1H)-one (Dess-Martin reagent) (0.223 g, 0.525 mmol) is added as a solid, together with anhydrous dichloromethane (1 mL). The resulting suspension is agitated for 1 h. The resin is then washed with dichloromethane, N,N-dimethylformamide, methanol and dichloromethane. The resin is dried in vacuo to afford the resin bound α-ketoamide.

EXAMPLE 6

Cleavage of a α-ketoamide from a Rink Resin

The dried resin-bound α-ketoamide from EXAMPLE 5 is treated with a cleavage system comprising trifluoroacetic acid (TFA)/dichloromethane/water/triisopropyl-silane (4/5.7/0.25/0.05) for 1 hour. The filtrate is collected and the solvent removed in vacuo.

The product is then purified by any convenient means, for example, by preparative HPLC.

The acylated resin-coupled α-hydroxyamide formed in EXAMPLE 4 can be removed by the same cleavage procedure outlined above in EXAMPLE 6.

What is claimed is:

1. A process for preparing a α-hydroxyamide, said process comprising the steps of:

a) reacting a resin which comprises a polymer-supported isocyanide having the formula:

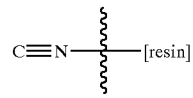

with an aldehyde having the formula:

in the presence of a catalyst, to form a resin-bound α-hydroxyamide having the formula:

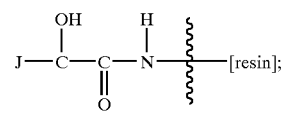

b) optionally oxidizing said resin-bound α-hydroxyamide to a α-ketoamide having the formula:

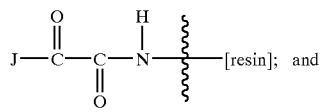

c) reacting said resin-bound α-hydroxyamide or α-ketoamide with a reagent which cleaves the nitrogen-resin bond to form a α-hydroxyamide having the formula:

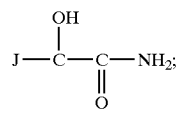

or α-ketoamide having the formula:

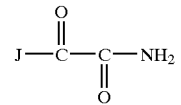

wherein J is a compatible organic radical which is not capable of reacting with said resin which comprises a polymer-supported isocyanide in step (a).

2. A process for preparing a α-hydroxyamide, said process comprising the steps of:

a) reacting a resin which comprises a polymer-supported isocyanide having the formula:

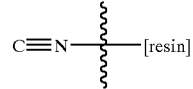

with an amino aldehyde having the formula:

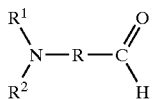

in the presence of a catalyst, to form a resin-bound α-hydroxyamide having the formula:

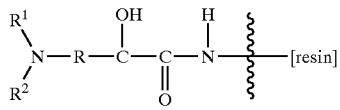

wherein R is a unit having the formula:

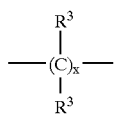

each $R^1$, $R^2$, and $R^3$ are independently hydrogen, $C_1$–$C_{20}$ substituted or unsubstituted hydrocarbyl, $C_1$–$C_{20}$ substituted or unsubstituted heterocyclic, and mixtures thereof; $R^1$ and $R^2$ can be taken together to form a single $C_1$–$C_{20}$ substituted or unsubstituted hydrocarbyl or $C_1$–$C_{20}$ substituted or unsubstituted heterocyclic unit; the index x is from 1 to 20; and b) reacting said resin-bound α-hydroxyamide with a reagent which cleaves the nitrogen-resin bond to form a α-hydroxyamide having the formula:

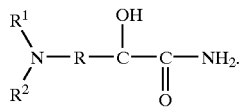

3. A process according to claim 2 wherein R is a unit having the formula:

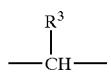

wherein $R^3$ is a unit selected from the group consisting of hydrogen, methyl, 1-methylethyl, 2-methylpropyl, 1-methylpropyl, amidomethyl, 2-amidoethyl, 2-mercaptoethyl, 2-methythioethyl, 3-guanidinopropyl, carboxymethyl, 2-carboxyethyl, 3-aminopropyl, 4-aminobutyl, hydroxymethyl, 1-hydroxyethyl, (4-imidazolyl)methyl, (3-indolyl)methyl, benzyl, 4-hydroxybenzyl, and mixtures thereof.

4. A process according to claim 2 wherein $R^1$ and $R^2$ are each independently hydrogen, $C_1$–$C_{12}$ hydrocarbyl, and mixtures thereof.

5. A process according to claim 2 wherein $R^1$ is hydrogen and $R^2$ is carbobenzyloxy, 9-fluorenylmethoxycarbonyl, 9-(2-sulfo)fluorenyl-methoxycarbonyl, or benzyl.

6. A process according to claim 2 wherein $R^1$ and $R^2$ are taken together to form a $C_1$–$C_{10}$ carbocyclic or heterocyclic ring.

7. A process according to claim 2 wherein said catalyst in step (a) is a system comprising trifluoroacetic acid and a base selected from the group consisting of substituted or unsubstituted pyridine, piperidine, lutidine, s-triazine, and salts thereof.

8. A process according to claim 2 wherein step (a) is conducted in the presence of a solvent.

9. A process according to claim 8 wherein said solvent is a non-polar aprotic solvent.

10. A process according to claim 9 wherein said solvent is selected from the group consisting of dichloromethane, dichloroethane, 1,1,1-trichloro-ethane, carbon tetrachloride, chloroform, benzene, toluene, xylene, and mixtures thereof.

11. A process according to claim 2 wherein step (a) is conducted at a temperature of from −78° C. to 25° C.

12. A process according to claim 11 wherein step (a) is conducted at a temperature of from −78° C. to 0° C.

13. A process according to claim 11 wherein step (a) is conducted at a temperature of from −15° C. to 25° C.

14. A process according to claim 13 wherein step (a) is conducted at a temperature of from −15° C. to 0° C.

15. A process according to claim 2 wherein step (a) is conducted in the presence of an inert atmosphere.

16. A process according to claim 2 wherein said reagent which cleaves the nitrogen-resin bond is a system comprising:
i) from 15% to 95% by weight, of trifluoroacetic acid; and
ii) a carbocation scavenger.

17. A process according to claim 16 wherein said scavenger is selected from the group consisting of dimethyl silane, triisopropylsilane, and mixtures thereof.

18. A process according to claim 2 wherein step (b) is conducted in the presence of a solvent.

19. A process according to claim 18 wherein said solvent is dichloromethane.

20. A process for preparing a α-ketoamide, said process comprising the steps of:
a) reacting a resin which comprises a polymer-supported isocyanide having the formula:

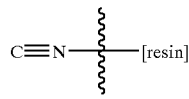

with an amino aldehyde having the formula:

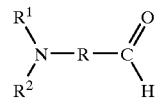

in the presence of a catalyst, to form a resin-bound α-hydroxyamide having the formula:

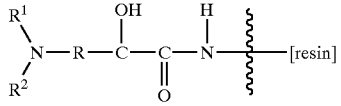

wherein R is a unit having the formula:

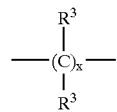

each $R^1$, $R^2$, and $R^3$ are independently hydrogen, $C_1$–$C_{20}$ substituted or unsubstituted hydrocarbyl, $C_1$–$C_{20}$ substituted or unsubstituted heterocyclic, and mixtures thereof; $R^1$ and $R^2$ can be taken together to form a single $C_1$–$C_{20}$ substituted or unsubstituted hydrocarbyl or $C_1$–$C_{20}$ substituted or unsubstituted heterocyclic unit; the index x is from 1 to 20;

b) reacting said resin-bound α-hydroxyamide with an oxidizing agent to form a resin-bound α-ketoamide having the formula:

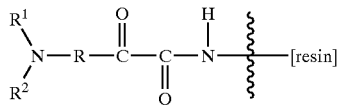

c) reacting said resin-bound α-ketoamide with a reagent which cleaves the nitrogen-resin bond to form a α-ketoamide having the formula:

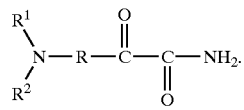

21. A process according to claim 20 wherein said catalyst in step (a) is a system comprising trifluoroacetic acid and a base selected from the group consisting of substituted or unsubstituted pyridine, piperidine, lutidine, s-triazine, and salts thereof.

22. A process according to claim 20 wherein step (a) is conducted in the presence of a solvent.

23. A process according to claim 22 wherein said solvent is a non-polar aprotic solvent.

24. A process according to claim 23 wherein said solvent is selected from the group consisting of dichloromethane, dichloroethane, 1,1,1-trichloro-ethane, carbon tetrachloride, chloroform, benzene, toluene, xylene, and mixtures thereof.

25. A process according to claim 20 wherein step (a) is conducted at a temperature of from −78° C. to 25° C.

26. A process according to claim 25 wherein step (a) is conducted at a temperature of from −78° C. to 0° C.

27. A process according to claim 25 wherein step (a) is conducted at a temperature of from −15° C. to 25° C.

28. A process according to claim 27 wherein step (a) is conducted at a temperature of from −15° C. to 0° C.

29. A process according to claim 20 wherein step (a) is conducted in the presence of an inert atmosphere.

30. A process according to claim 20 wherein said oxidizing agent in step (b) is selected from the group consisting of Dess-Martin periodate, pyridine sulfoxide, TEMPO, sodium hypochlorite, pyridinium dichromate, pyridinium chlorochromate, DMSO/oxalyl chloride, DDQ, and mixtures thereof.

31. A process according to claim 20 wherein said reagent which cleaves the nitrogen-resin bond in step (c) is a system comprising:
  i) from 15% to 95% by weight, of trifluoroacetic acid; and
  ii) a carbocation scavenger.

32. A process according to claim 31 wherein said scavenger is selected from the group consisting of dimethyl silane, triisopropylsilane, and mixtures thereof.

33. A process according to claim 20 wherein step (c) is conducted in the presence of a solvent.

34. A process according to claim 20 wherein said solvent is dichloromethane.

* * * * *